US009763784B2

(12) United States Patent
Bielefeld

(10) Patent No.: US 9,763,784 B2
(45) Date of Patent: *Sep. 19, 2017

(54) TOOL FOR THE ADJUSTMENT OF A PROSTHETIC ANATOMICAL DEVICE

(75) Inventor: Eric E. Bielefeld, Floyds Knobs, IN (US)

(73) Assignee: St. Jude Medical, Inc., St. Paul, MN (US)

( * ) Notice: Subject to any disclaimer, the term of this patent is extended or adjusted under 35 U.S.C. 154(b) by 839 days.

This patent is subject to a terminal disclaimer.

(21) Appl. No.: 13/982,531

(22) PCT Filed: Jan. 31, 2012

(86) PCT No.: PCT/US2012/023349
§ 371 (c)(1),
(2), (4) Date: Nov. 12, 2013

(87) PCT Pub. No.: WO2012/106351
PCT Pub. Date: Aug. 9, 2012

(65) Prior Publication Data
US 2014/0088691 A1   Mar. 27, 2014

Related U.S. Application Data

(60) Provisional application No. 61/438,129, filed on Jan. 31, 2011, provisional application No. 61/527,801, filed on Aug. 26, 2011.

(51) Int. Cl.
*A61F 2/24* (2006.01)
*B25B 15/02* (2006.01)
(Continued)

(52) U.S. Cl.
CPC .......... *A61F 2/2466* (2013.01); *A61F 2/2496* (2013.01); *B25B 15/02* (2013.01);
(Continued)

(58) Field of Classification Search
CPC .... A61F 2/2466; A61F 2/2496; A61F 2/2445; A61F 2250/001; B25B 23/0064; B25B 15/02; B25G 3/18; B25G 1/046
See application file for complete search history.

(56) References Cited

U.S. PATENT DOCUMENTS 2,810,415 A   10/1957   Johnson
4,099,518 A   7/1978    Baylis et al.
(Continued)

FOREIGN PATENT DOCUMENTS

DE   4441965 C1    6/1996
DE   19832303 A1   1/2000
(Continued)

OTHER PUBLICATIONS

Extended European Search Report for Application No. EP16181026.2 dated Oct. 27, 2016.
(Continued)

*Primary Examiner* — Richard Louis
(74) *Attorney, Agent, or Firm* — Lerner, David, Littenberg, Krumholz & Mentlik, LLP

(57) ABSTRACT

An adjustment tool enables manipulation of a prosthetic anatomical device such as an annuloplasty ring. The tool includes a compression member which is operative for retarding rotation of the adjustment shaft to preclude inadvertent rotation thereof during use of the tool by the surgeon. A locking device is associated with the adjustment tool to enable the releasable attachment of the tool to the anatomical device during its adjustment by manipulation of the tool. The locking device is oriented into operative and inoperative positions by the engagement and disengagement of locking elements. A scale may be provided on the adjustment tool to
(Continued)

assist a surgeon in determining the size or amount of adjustment to the size of the anatomical device during its adjustment.

21 Claims, 9 Drawing Sheets

(51) Int. Cl.
    *B25G 1/04* (2006.01)
    *B25G 3/18* (2006.01)
    *B25B 23/00* (2006.01)
(52) U.S. Cl.
    CPC .......... *B25B 23/0064* (2013.01); *B25G 1/046* (2013.01); *B25G 3/18* (2013.01); *A61F 2/2445* (2013.01); *A61F 2250/001* (2013.01)

(56) References Cited

U.S. PATENT DOCUMENTS

| | | | |
|---|---|---|---|
| 5,257,632 A | 11/1993 | Turkel et al. | |
| 5,605,080 A | 2/1997 | Pfefferle et al. | |
| 5,685,206 A | 11/1997 | Ma | |
| 6,019,776 A | 2/2000 | Preissman et al. | |
| 6,086,543 A | 7/2000 | Anderson et al. | |
| 6,090,138 A | 7/2000 | Chasak et al. | |
| 6,110,128 A | 8/2000 | Andelin et al. | |
| 6,117,108 A | 9/2000 | Woehr et al. | |
| 6,189,422 B1 | 2/2001 | Stihl | |
| 6,221,047 B1 | 4/2001 | Greene et al. | |
| 6,312,394 B1 | 11/2001 | Fleming, III | |
| 6,554,778 B1 | 4/2003 | Fleming, III | |
| 6,616,630 B1 | 9/2003 | Woehr et al. | |
| 6,645,213 B2 | 11/2003 | Sand et al. | |
| 6,689,102 B2 | 2/2004 | Greene | |
| 6,893,184 B2 | 5/2005 | Mills et al. | |
| 7,175,660 B2 | 2/2007 | Cartledge et al. | |
| 7,442,207 B2 | 10/2008 | Rafiee | |
| 7,455,690 B2 | 11/2008 | Cartledge et al. | |
| 7,658,725 B2 | 2/2010 | Bialecki et al. | |
| 7,850,620 B2 | 12/2010 | Miller et al. | |
| 8,486,024 B2 | 7/2013 | Steube | |
| 8,574,289 B2 | 11/2013 | Cartledge et al. | |
| 8,628,497 B2 | 1/2014 | Finnestad et al. | |
| 8,715,250 B2 | 5/2014 | Tremblay | |
| 8,758,372 B2 | 6/2014 | Cartledge et al. | |
| 8,778,021 B2 | 7/2014 | Cartledge | |
| 8,834,422 B2 | 9/2014 | Walker et al. | |
| 9,107,750 B2 | 8/2015 | Cartledge et al. | |
| 9,138,316 B2 | 9/2015 | Bielefeld | |
| 2001/0049558 A1 | 12/2001 | Liddicoat et al. | |
| 2003/0057665 A1* | 3/2003 | Matney .................. | A63C 17/04 280/11.231 |
| 2003/0125715 A1 | 7/2003 | Kuehn et al. | |
| 2003/0191416 A1 | 10/2003 | Rosenman et al. | |
| 2004/0034410 A1 | 2/2004 | Holmberg | |
| 2005/0027263 A1 | 2/2005 | Woehr et al. | |
| 2005/0222665 A1* | 10/2005 | Aranyi .................. | A61B 17/068 623/1.11 |
| 2005/0222678 A1 | 10/2005 | Lashinski et al. | |
| 2005/0257345 A1 | 11/2005 | Mitchell et al. | |
| 2006/0064164 A1 | 3/2006 | Thelen et al. | |
| 2006/0217803 A1 | 9/2006 | Ingle et al. | |
| 2006/0233602 A1 | 10/2006 | Merems | |
| 2006/0241748 A1 | 10/2006 | Lee et al. | |
| 2007/0039425 A1 | 2/2007 | Wang | |
| 2007/0239108 A1 | 10/2007 | Albrecht et al. | |
| 2008/0033545 A1 | 2/2008 | Bergin | |
| 2008/0045857 A1 | 2/2008 | Miller et al. | |
| 2008/0287859 A1 | 11/2008 | Miller et al. | |
| 2008/0308600 A1 | 12/2008 | Kana | |
| 2009/0125102 A1 | 5/2009 | Cartledge et al. | |
| 2009/0192605 A1 | 7/2009 | Gloss et al. | |
| 2009/0194446 A1 | 8/2009 | Miller et al. | |
| 2009/0259305 A1 | 10/2009 | Lane et al. | |
| 2009/0266367 A1 | 10/2009 | Ziv et al. | |
| 2009/0275994 A1 | 11/2009 | Phan et al. | |
| 2010/0004626 A1 | 1/2010 | Miller et al. | |
| 2010/0010538 A1 | 1/2010 | Juravic et al. | |
| 2010/0011535 A1 | 1/2010 | Schuelke | |
| 2010/0016804 A1 | 1/2010 | Muskatello et al. | |
| 2010/0076503 A1 | 3/2010 | Beyar et al. | |
| 2010/0161047 A1 | 6/2010 | Cabiri | |
| 2010/0168675 A1 | 7/2010 | Cindrich et al. | |
| 2010/0211166 A1 | 8/2010 | Miller et al. | |
| 2010/0222746 A1 | 9/2010 | Burkholz | |
| 2011/0000347 A1 | 1/2011 | Stark | |
| 2011/0015617 A1 | 1/2011 | Chesnin et al. | |
| 2011/0066231 A1 | 3/2011 | Cartledge et al. | |
| 2011/0082387 A1 | 4/2011 | Miller et al. | |
| 2011/0190879 A1 | 8/2011 | Bobo et al. | |
| 2011/0202130 A1 | 8/2011 | Cartledge et al. | |
| 2011/0295262 A1 | 12/2011 | Germain et al. | |
| 2011/0301551 A1 | 12/2011 | Koehler et al. | |
| 2012/0065590 A1 | 3/2012 | Bierman et al. | |
| 2012/0090863 A1 | 4/2012 | Puzio et al. | |
| 2012/0136436 A1 | 5/2012 | Cabiri et al. | |
| 2012/0144626 A1 | 6/2012 | Lanz | |
| 2013/0006232 A1 | 1/2013 | Pellegrino et al. | |
| 2013/0116693 A1 | 5/2013 | Nelson et al. | |
| 2014/0074226 A1 | 3/2014 | Bielefeld et al. | |
| 2014/0213931 A1 | 7/2014 | Lee | |
| 2015/0142048 A1 | 5/2015 | Coleman et al. | |
| 2015/0150541 A1 | 6/2015 | Fumex et al. | |
| 2015/0230823 A1 | 8/2015 | Morgan et al. | |
| 2015/0290430 A1 | 10/2015 | Koehler et al. | |
| 2016/0000017 A1 | 1/2016 | Pringnitz | |

FOREIGN PATENT DOCUMENTS

| | | |
|---|---|---|
| DE | 20015842 U1 | 11/2000 |
| DE | 202005013648 U1 | 3/2006 |
| WO | 0149245 A2 | 7/2001 |
| WO | 0150985 A1 | 7/2001 |
| WO | 2008/085814 A2 | 7/2008 |
| WO | 2008097999 A2 | 8/2008 |
| WO | 2009126629 A1 | 10/2009 |
| WO | 2010014671 A1 | 2/2010 |
| WO | 2010073246 A2 | 7/2010 |

OTHER PUBLICATIONS

International Search Report and Written Opinion for Application No. PCT/US2012/023359 dated May 11, 2013.
International Search Report for Application No. PCT/US2012/023309 dated Jun. 20, 2012.
International Search Report for Application No. PCT/US2012/023340 dated Jun. 4, 2012.
International Search Report for Application No. PCT/US/2012/023349 dated Jun. 18, 2012.
International Search Report for Application No. PCT/US2012/023333 dated May 10, 2012.

* cited by examiner

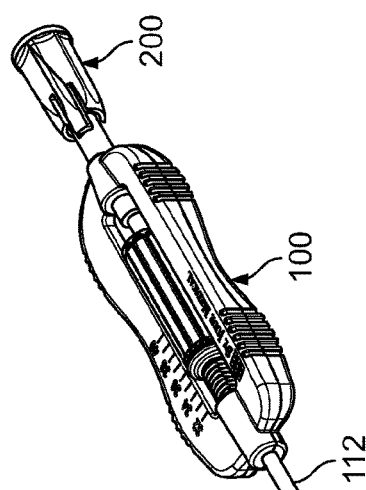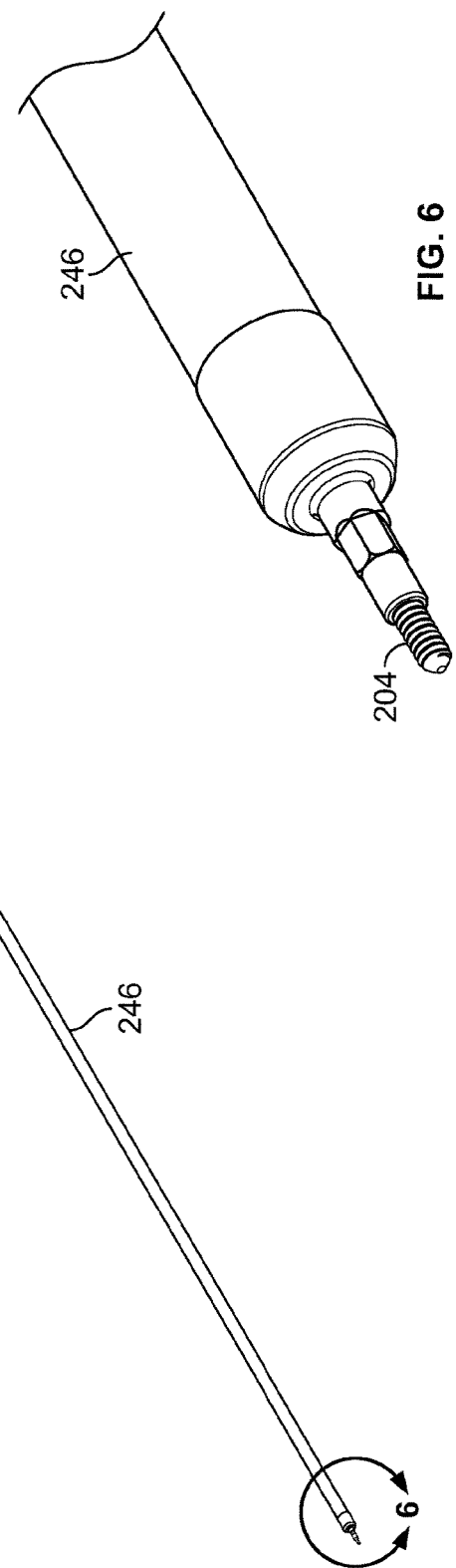

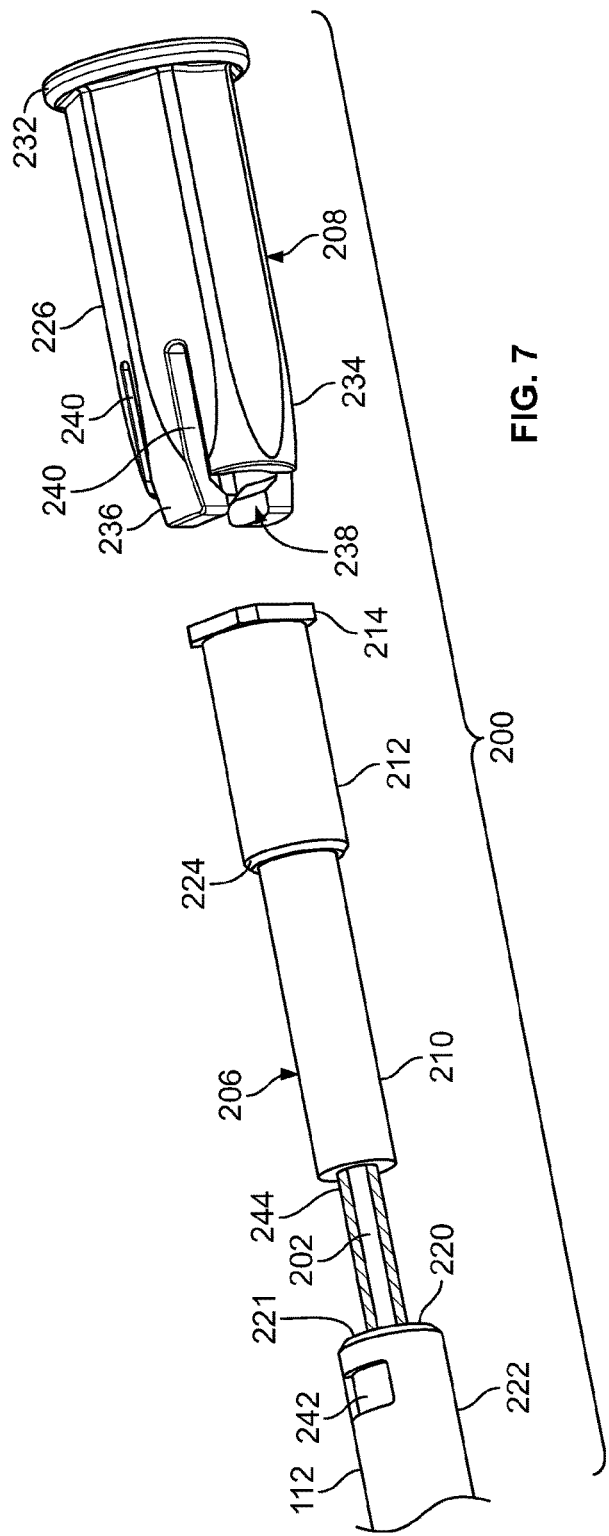
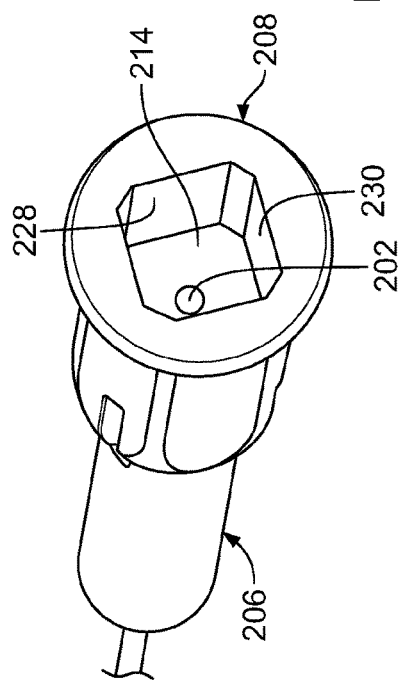

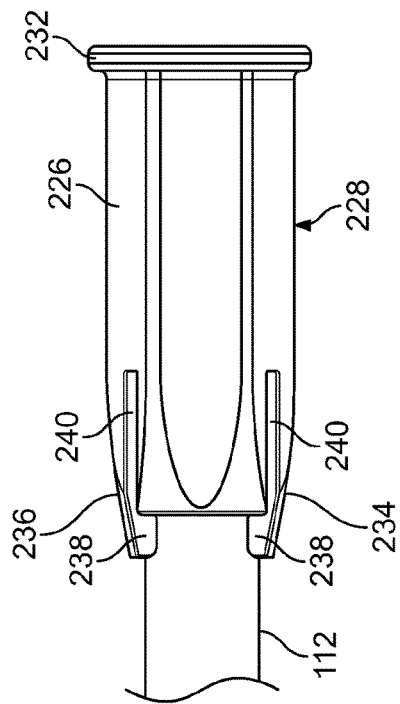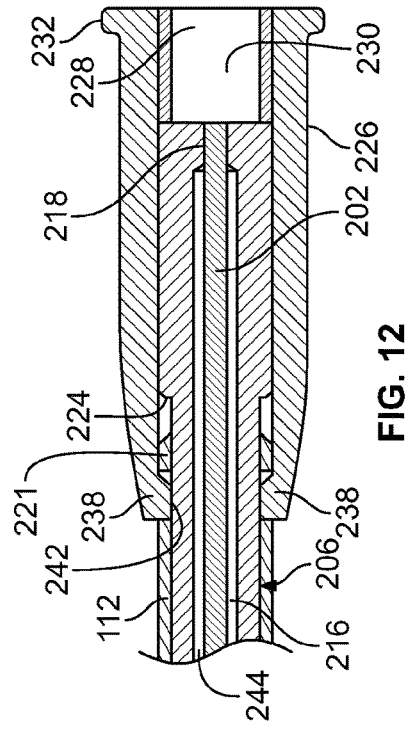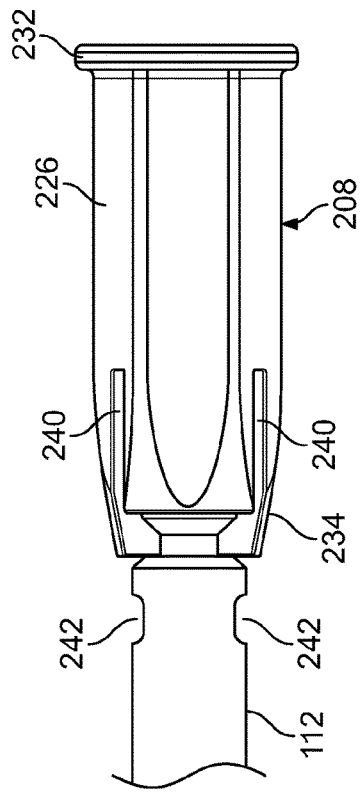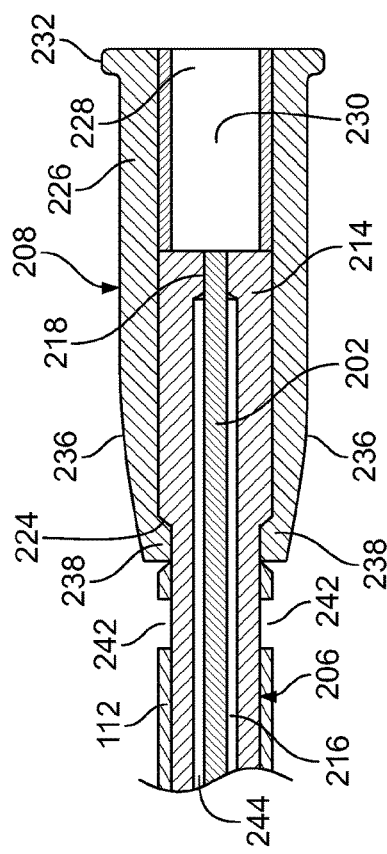

TOOL FOR THE ADJUSTMENT OF A PROSTHETIC ANATOMICAL DEVICE

CROSS-REFERENCE TO RELATED APPLICATIONS

This application is a national phase entry under 35 U.S.C. §371 of International Application No. PCT/US2012/023349 filed Jan. 31, 2012, published in English, which claims the benefit of the filing dates of U.S. Provisional Patent Application No. 61/438,129 filed Jan. 31, 2011 and of U.S. Provisional Patent Application No. 61/527,801 filed Aug. 26, 2011, the entire disclosures of which are each hereby incorporated herein by reference.

BACKGROUND OF THE INVENTION

The present invention relates in general to a tool for adjusting a prosthetic anatomical device, and more particularly, to a tool for adjusting the Seguin size and/or shape of an implantable device.

Heart valve disease is a condition in which one or more valves of the heart fail to function properly. Diseased heart valves may be categorized as either stenotic, wherein the valve does not open sufficiently to allow adequate forward flow of blood through the valve, or incompetent, wherein the valve does not close completely causing excessive backward flow of blood through the valve when the valve is closed.

By way of one specific example, the mitral valve is the inflow valve for the left side of the heart. Blood flows from the lungs, where it picks up oxygen, through the pulmonary veins, to the left atrium of the heart. After the left atrium fills with blood, the mitral valve allows blood to flow from the left atrium into the heart's main pumping chamber called the left ventricle. It then closes to keep blood from leaking back into the left atrium or lungs when the left ventricle contracts to push blood out to the body.

Valve disease relating to the mitral valve often involves secondary mitral regurgitation which is the backward flow of blood from the left ventricle to the left atrium resulting from imperfections in the mitral valve. One repair technique for treating regurgitation is called annuloplasty, in which the size and/or shape of the valve annulus is modified by securing a prosthetic adjustable annuloplasty ring to an interior wall of the heart around the valve annulus. The size and/or shape of the annuloplasty ring is adjusted in situ for maintaining coaptation to prevent reversed blood flow.

Examples of an adjustable annuloplasty ring are disclosed in United States Patent Application Publication No. 2011/0066231, the disclosure of which is incorporated herein by reference. The disclosed annuloplasty ring includes an adjustment assembly for expanding or contracting the Seguin size of the opening formed by the ring. A suitable tool is also disclosed to engage the adjustment assembly to enable adjustment of the annuloplasty ring in situ once implanted into a patient.

SUMMARY OF THE INVENTION

The present invention discloses a minimally invasive adjustment tool having enhanced features to enable the in situ adjustment of an annuloplasty ring or other prosthetic anatomical device after being implanted into a patient.

In accordance with one embodiment, the adjustment tool of the present invention incorporates a hand held handle which rotationally supports a center shaft or hypotube which is operative for adjusting the opening or Seguin size and/or shape of an adjustable device, for example, an anatomical structure such as an annuloplasty ring. The hypotube is rotated by an internally threaded knob received about an externally threaded cylinder. The knob is accessible to the surgeon through an enlarged opening within the handle. A compression member is arranged within the housing for engaging a portion of the hypotube for retarding its unrestricted rotation when the tool is being used for adjustment of an anatomical device such as an annuloplasty ring and the like.

In accordance with a further embodiment of the present invention, the tool can incorporate a rotational locking device which is adapted for releasably attaching the tool to the prosthetic anatomical device to be adjusted. The locking device incorporates an elongated shaft having a threaded end received within the hypotube, and optionally within a second hypotube concentrically arranged within the first hypotube. A knob is coupled to one end of the first hypotube and attached to an end of the shaft. A sleeve is slidably engaged about the knob in keyed relationship between a first and second position. The first hypotube adjacent its proximal end is provided with a first locking element and the sleeve is provided with a second locking element. Movement of the sleeve to the first position engages the locking elements thereby precluding rotation of the sleeve and preventing rotation of the shaft. Movement of the sleeve to the second position disengages the first and second locking elements whereby rotation of the sleeve causes rotation of the shaft and its threaded end relative to the anatomical device.

In accordance with a further embodiment of the present invention there is described a tool for manipulating an adjustable device which includes a cylinder, a knob rotationally engaged about the cylinder, a shaft extending through the cylinder coupled to the knob, whereby rotation of the knob about the cylinder causes rotation of the shaft, a housing supporting the shaft for rotation by the knob, and a member arranged within the housing engaging a portion of the shaft for retarding rotation of the shaft.

In accordance with the above embodiment, the member in the nature of a compression member comprises a plurality of appendages arranged circumferentially about the shaft, and further includes an o-ring arranged about the plurality of appendages, wherein the o-ring provides a compressive force compressing the plurality of appendages against the shaft for retarding rotation of the shaft. The compression member and the cylinder may be a one piece integral unit. At least one tab extends from the cylinder in engagement with a portion of the housing, the at least one tab preventing rotation of the cylinder upon rotation of the knob thereabout.

In accordance with the above embodiment, the housing is in the nature of a handle having opposing ends and an elongated opening therebetween, a first bore extending through one end of the handle in communication with the opening and a second bore extending through another end of the handle in communication with the opening. The plurality of appendages and the o-ring are arranged within the first bore of the handle. One end of the shaft is rotationally supported in the first bore and another end of the shaft is rotationally supported in the second bore.

More particularly, the present invention describes in accordance with another embodiment a tool for manipulating an adjustable device which includes an externally threaded elongated barrel having a distal end and a proximal end, an internally threaded knob rotationally coupled about the barrel, a shaft extending through the barrel having a portion thereof attached to the knob, whereby rotation of the knob causes rotation of the shaft, a compression member extending from the distal end of the barrel overlaying the shaft, a compression element compressing the compression member against the shaft, whereby rotation of the shaft is retarded, and a housing supporting the rotation of the shaft by rotation of the knob.

In accordance with the above embodiment, the compression member is in the nature of a plurality of appendages arranged circumferentially about the shaft, and the compression element is in the nature of an o-ring arranged about the plurality of appendages, wherein the o-ring provides a compressive force compressing the plurality of appendages against the shaft for retarding rotation of the shaft. The compression member and the barrel may be a one piece integral unit. At least one tab extends from the barrel in engagement with a portion of the housing, the at least one tab preventing rotation of the barrel upon rotation of the knob thereabout.

In accordance with the above embodiment, the housing is in the nature of a handle having opposing ends and an elongated opening therebetween, a first bore extending through one end of the handle in communication with the opening and a second bore extending through another end of the handle in communication with the opening. The compression member and compression element are arranged with the first bore of the handle. One end of the shaft is rotationally supported in the first bore and another end of the shaft is rotational supported in the second bore.

Still more particularly, the present invention describes in accordance with another embodiment, an adjustment tool for adjusting the size of an annuloplasty ring, the tool includes a handle having a distal end and a proximal end, the handle having an elongated central opening, a first bore extending through the distal end of the handle in communication with the opening, and a second bore extending through the proximal end in communication with the opening, an externally threaded hollow barrel arranged within the opening of the handle, the barrel having a fixed axis in alignment with the first and second bores, an internally threaded knob rotationally engaged about the barrel within the opening, the knob having a rotational axis in alignment with the fixed axis of the barrel, a central shaft extending along the rotational axis through the first bore and through the barrel into the knob, the shaft having a portion attached to the knob whereby rotation of the knob about the barrel causes rotation of the shaft about the rotational axis, a plurality of appendages extending from the barrel into the first bore surrounding at least a portion of the shaft, and a compression element compressing the plurality of appendages about the shaft whereby rotation of the shaft is retarded.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects and advantages thereof may best be understood by reference to the following detailed description when read with the accompanying drawings in which:

FIG. 5 is a perspective view of the assembled adjustment tool coupled to an elongated shaft having its distal end constructed to operatively engage an adjustment mechanism on an annuloplasty ring.

FIG. 6 is an enlarged perspective view of the distal end of the adjustment tool shaft constructed to operatively engage the adjustment mechanism of an annuloplasty ring.

FIG. 7 is an exploded perspective view showing the components of a rotational locking device in accordance with one embodiment of the present invention in a disassembled arrangement.

FIG. 8 is a perspective view showing the assembly of the proximal end of the rotational locking device as shown in FIG. 10.

FIG. 9 is a front elevational view of an assembled rotational locking device as shown in FIG. 7 arranged in an unlocked position.

FIG. 10 is a cross-sectional view of the assembled rotational locking device as shown in FIG. 9 in an unlocked position.

FIG. 11 is a front elevational view of an assembled rotational adjustment device as shown in FIG. 7 in a locked position.

FIG. 12 is a cross-sectional view of the assembled rotational locking device as shown in FIG. 11 in a locked position.

DETAILED DESCRIPTION

Figure 1:
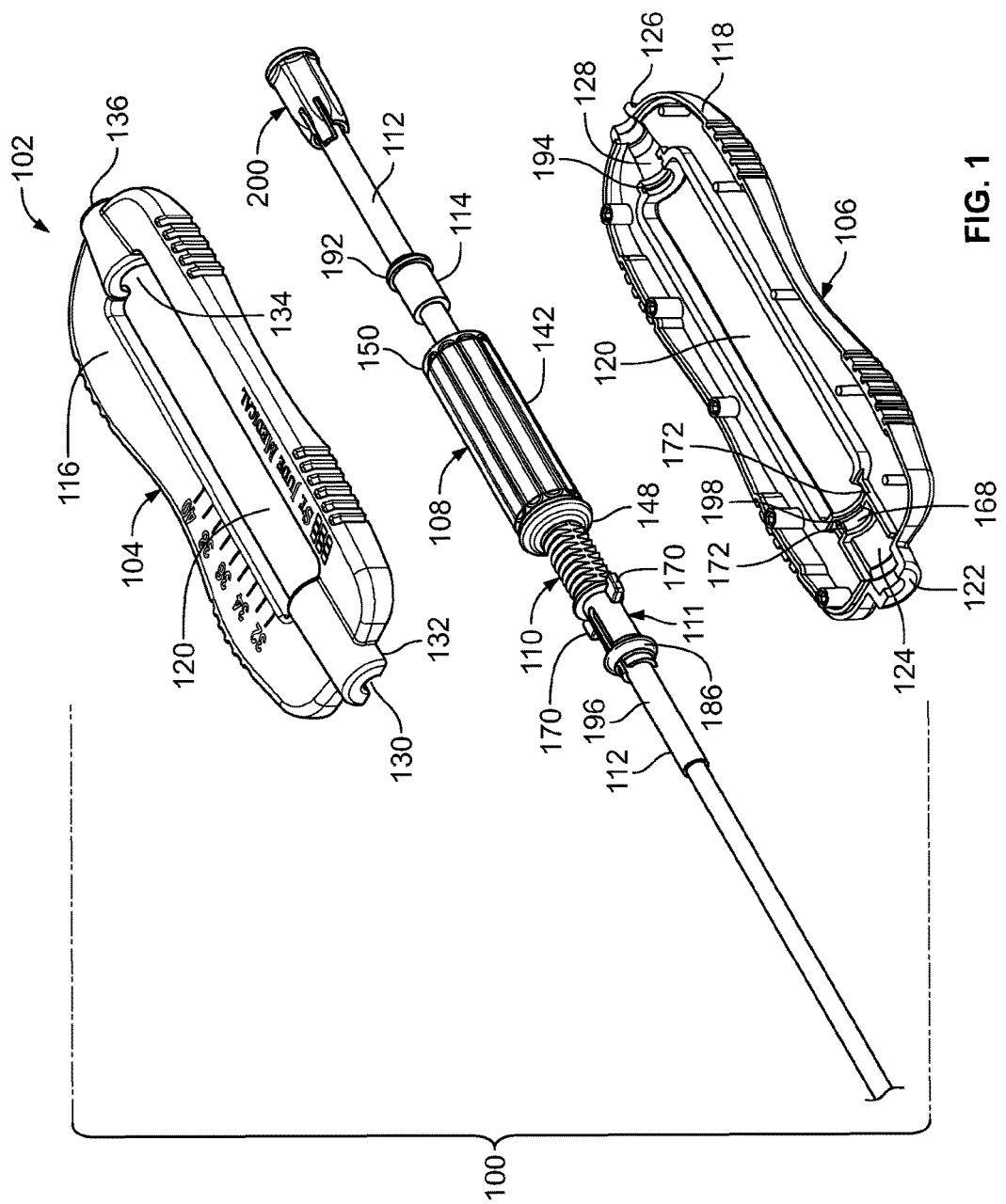
FIG. 1 is an exploded perspective view showing the components of an adjustment tool in accordance with one embodiment of the present invention in a partially assembled arrangement.

In describing the preferred embodiments of the invention illustrated in the drawings, specific terminology will be used for the sake of clarity. However, the invention is not intended to be limited to the specific terms so used, and it is to be understood that each specific term includes all equivalence that operate in a similar manner to accomplish a similar purpose.

As used herein, the terms "proximal" and "distal" are to be taken as relative to a user (e.g., a surgeon) using the disclosed device. "Proximal" is to be understood as relatively close to the user and "distal" is to be understood as relatively farther away from the user.

Referring to the drawings, wherein like reference numerals represent like elements, there is shown in FIG. 1 an adjustment tool 100 constructed in accordance with one embodiment of the present invention. The adjustment tool 100 in the illustrated embodiment is constructed generally to include a housing 102 formed from a first housing half 104 and a mating second housing half 106; an elongated knob 108; an elongated cylinder such as a barrel 110; a compression member 111; an elongated central shaft 112 such as an elongated hypotube; and an optional bushing 114. A detailed description of the aforementioned components of the adjustment tool 100 and their assembled relationship will now be described.

Figure 2:
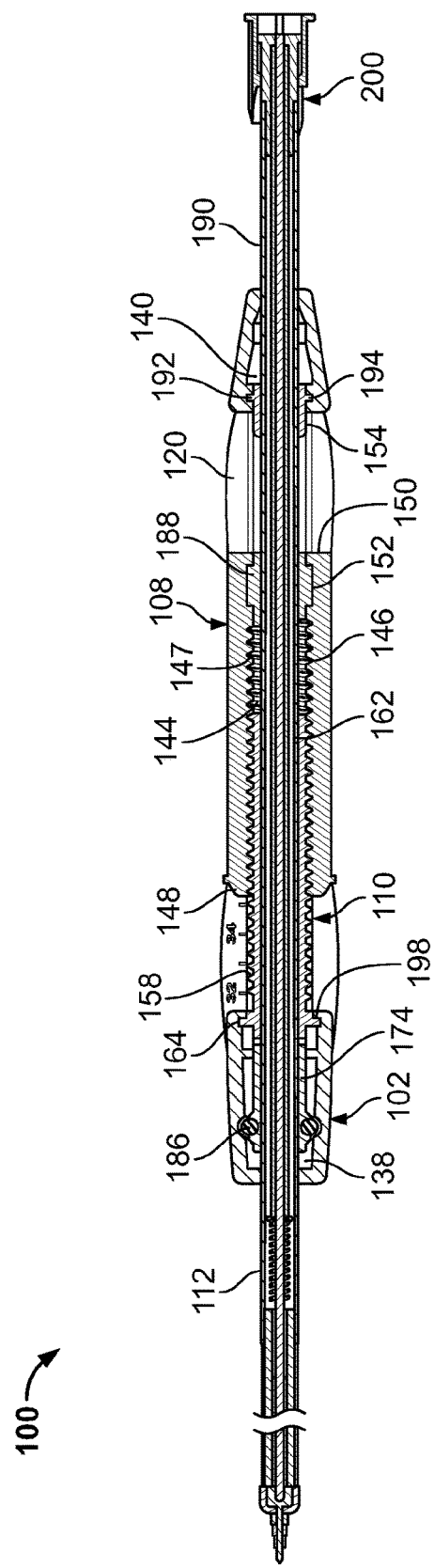
FIG. 2 is a cross-sectional view of the assembled adjustment tool taken along line 2-2 in FIG. 4.

Referring to FIGS. 1 through 4, the first and second housing halves 104, 106 which form the housing 102 are generally constructed as complimentary elongated annular shaped hollow shells 116, 118. When, assembled, the housing halves 104, 106 form a central elongated opening 120. The first housing half 104 is provided with a through bore 130 at its distal end 132, and a through bore 134 at its proximal end 136. In a complimentary construction, the second housing half 106 at its distal end 122 is formed with a through bore 124, and at its proximal end 126 with a through bore 128. The assembled relationship of the first and second housing halves 104, 106 is best shown in FIG. 2. When assembled to form the housing 102, corresponding bores 124, 130 at the distal ends 122, 132 of the housing halves form a central bore 138. Likewise, the corresponding bores 128, 134 at the proximal ends 126, 136 of the housing halves form a central bore 140. As previously described, the first and second housing halves 104, 106, when assembled, form the elongated central opening 120 within the adjustment tool 100 in communication with each of the bores 138, 140.

The knob 108 can be constructed as an elongated cylindrical body 142 having a central longitudinally extending through bore 144 surrounded by a threaded portion 146 formed from a plurality of threads 147. The threaded portion 146 generally extends from the distal end 148 of the knob 108 to adjacent its proximal end 150. An annular internal recess 152 is formed circumscribing the bore 144 adjacent the proximal end 150 of the knob. The outer surface of the knob 108 may be textured to provide a friction or irregular surface to facilitate rotation of the knob by the surgeon's fingers during use of the adjustment tool 100.

Figure 3:
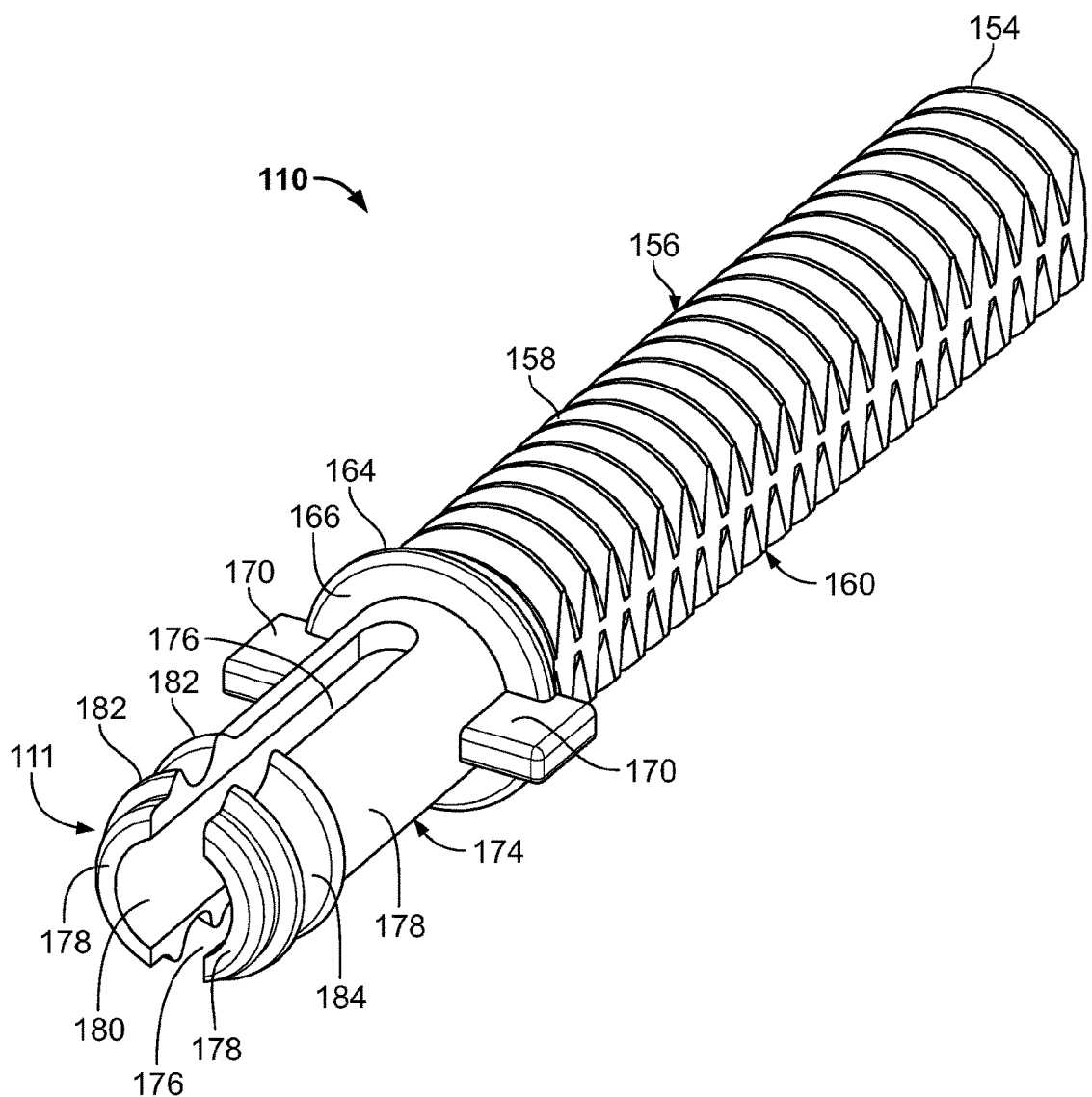
FIG. 3 is a perspective view of an elongated externally threaded barrel forming one component of the adjustment tool.

The barrel 110 as best shown in FIG. 3 can be formed as an elongated cylindrical body 154 having an externally threaded portion 156 formed by a plurality of threads 158. The threaded portion 156 may have one or more flatten regions 160 extending longitudinally along the length of the barrel at one or more circumferential locations. The flatten region functions to facilitate the molding process when forming the barrel 110 from polymer compositions. A bore 162 extends longitudinally through the center of the body 154. A large diameter circumscribing ring 164 can be provided at the distal end 166 of the body 154. The ring 164 is captured within a corresponding confining opening 168 provided within the distal end of the adjustment tool 100 for securing the barrel 110 and preventing its longitudinal movement within the housing 102.

One or more protrusions 170 in the nature of flanges or other such structures may be provided extending radially outward about a circumferential portion of the distal end 166 outwardly of the ring 164. In accordance with one embodiment as illustrated in FIG. 3, two protrusions 170 are arranged opposing one another extending outwardly. The protrusions 170 are adapted to be received within confining notches 172 formed by the mating first and second housing halves 104, 106 adjacent the opening 168. The protrusions 170 by being captured within the notches 172 prevent rotation of the barrel 110 during use of the tool 100, while the ring 164 prevents longitudinal movement of the barrel within the opening 120 formed within the housing 102.

Although the protrusions 170 have been described as flanges, the protrusions may take any other shape or form which functions to cooperate with the housing 102 to prevent rotation of the barrel. In addition, although two protrusions 170 have been illustrated, it is contemplated that only one protrusion would be sufficient to prevent rotation of the barrel. Further, any greater number of protrusions 170 can be provided, such as three or more protrusions in the form of flanges or other structures as thus far described and contemplated.

The compression member 111 is arranged extending longitudinally outwardly from the distal end 166 of the barrel 110. The compression member 111, in accordance with one embodiment, is constructed from an elongated cylindrical body 174 having one or more circumferentially arranged elongated slots 176 dividing the body into a plurality of elongated flexible members 178 in the nature of finger like appendages. A through bore 180 is provided longitudinally through the compression member 111 in communication with the bore 162 provided within the barrel 110. The inner surfaces of the members 178 may be shaped and sized to conform to and be arranged in surface contact with the outer surface of the central shaft 112. The primary function of the compression member 111 is to retard rotation of the central shaft 112 so as to prevent its free unintended rotation during use of the adjustment tool 100 by creating frictional engagement of the members 178 with the central shaft. This can be accomplished, in one embodiment, by providing one or more elongated slots 176 which enable each member 178 to be sufficiently flexible so as to be arrangeable in compressive engagement with the central shaft 112.

The compression member 111 may be constructed to include any number of elongated members 178 by providing one or more elongated slots 176. Although two slots 176 are illustrated, it is contemplated that a single slot would be sufficient to provide the body 174 with sufficient flexibility to be compressively engaged about the shaft 112 to retard its rotation. Further by way of example, three elongated members 178 may be provided by incorporating three elongated slots 176 arranged circumferentially about the cylindrical body 174. It is not required that the slots 176 be equally spaced circumferentially about the body 174.

Compression of the elongated members 178 against the central shaft 112 may be accomplished in a number of ways. In the preferred embodiment, the end of the cylindrical body 174 can be provided with a pair of spaced apart circumscribing ribs 182 forming an annular opening 184 therebetween. A resilient o-ring 186 can be received within the annular opening 184 to provide a uniform inward compressive force of the elongated members 178 against the external surface of the central shaft 112. The degree of force applied by the o-ring 186 can be predetermined by the relative size of the o-ring to that of the annular opening 184. Accordingly, one can design the compression member 111 to apply a predetermined degree of force against the shaft 112 depending upon the selective size of the o-ring 186. In another embodiment, for example, the inside diameter of the bore 180 may be slightly smaller than the outside diameter of the shaft 112 to provide the compressive force.

In accordance with the preferred embodiment, the compression member 111 is integrally formed with the barrel 110 as a one piece unitary construction. It is contemplated that the compression member 111 and barrel 110 will be molded from suitable synthetic polymers such as ABS (Acrylonitrile butadiene styrene), nylon, Acetyl, polycarbonate, PBT (Polybutylene Terephthalate), and/or other suitable polymers.

In accordance with another embodiment, it is contemplated that the compression member 111 may be formed as a separate component from the barrel 110, and secured thereto by any suitable means, such as mechanical, adhesive or thermal bonding. One advantage of a two piece construction allows the compression member 111 to be formed from materials different from the materials of the barrel 110. In this regard, the separate compression member 111 can be formed from materials which have a greater degree of resiliency and/or flexibility than would generally be used for construction of the barrel 110 which requires a plurality of threads 158 for supporting rotation of the knob 108. Constructing the compression member 111 of softer and/or more resilient materials, may enable greater control of the compressive force of the compression member against the central shaft 112.

In accordance with other embodiments of the present invention, the compression member can be constructed from other elements and structure provided within the bore 138 at the distal end of the housing 102 which will compressively engage the central shaft 112 extending therethrough or otherwise effect retardation of its rotation. For example, as previously discussed, one embodiment may include an interference fit between the central shaft 112 and the barrel 110, without a compression member. In this embodiment, the natural inner diameter of the barrel 110 is smaller than the outer diameter of the central shaft 112, such that the barrel 110 is resiliently deformed from its undeformed size and/or shape when the central shaft 112 is inserted therein, providing an interference fit between the central shaft 112 and the barrel 110. Such an interference fit enhances the frictional engagement between the barrel 110 and the central shaft 112.

Figure 16:
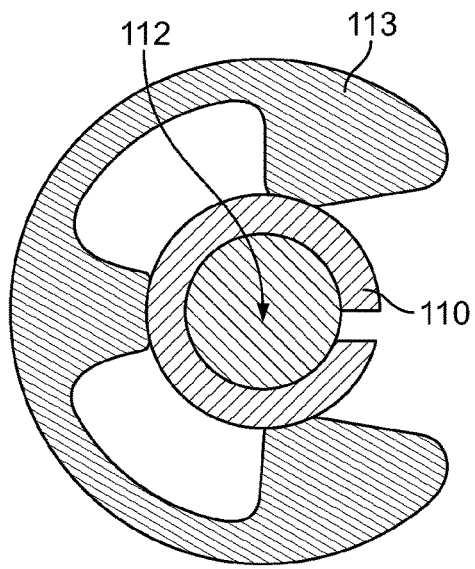
FIG. 16 is a cross-sectional view of a barrel in engagement with the elongated shaft and a fastener along a longitudinal axis thereof in accordance with one embodiment of the present invention.

According to another embodiment, a spring-like fastener 113 may be used instead of an o-ring. (See FIG. 16.) In the illustrative embodiment shown, the spring-like fastener 113 is an e-clip. Preferably, the spring-like fastener 113 is made of a metal, but may in other embodiments be made of any other suitable resilient material, such as a rubber, a polymer, or a plastic material, including, without limitation, the synthetic polymers disclosed above with respect to the barrel 110 and compression member 111.

Figure 17:
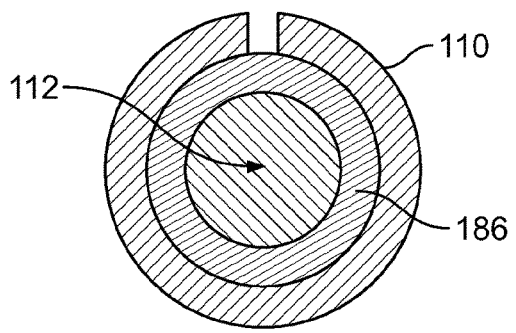
FIG. 17 is a cross-sectional view of an o-ring in engagement with an elongated shaft and a barrel a longitudinal axis thereof in accordance with another embodiment of the present invention.

Another embodiment includes the o-ring 186 being in direct contact with the central shaft 112 and being captured by the barrel 110, such that the o-ring 186 frictionally engages the central shaft and the barrel. In such an embodiment, the barrel 110 is capable of trapping the o-ring 186 in its relative location by virtue of the friction therebetween. (See FIG. 17.)

A proximal portion of the central shaft 112 is fixedly attached to the proximal end 150 of the knob 108. In accordance with one embodiment, the knob 108 is constructed from synthetic polymers such as from those which form the barrel 110. The central shaft 112 can be constructed from suitable biocompatible metals such as stainless steel, titanium and the like. A similar metal insert 188 can be molded into the annular recess 152 formed in the proximal end 150 of the knob 108. The shaft 112 can be welded to the insert 188 or by using other suitable fusion techniques. In accordance with another embodiment, the knob 108 can be constructed from similar metal materials as the central shaft 112. In this event, the shaft 112 can be welded directly to the knob 108. Based upon on the foregoing construction, rotation of the knob 108 causes corresponding rotation of the central shaft 112.

The central shaft 112 extends through the compression member 111, through the barrel 110, and through the knob 108, where a portion thereof is attached to the proximal end 150 of the knob. The proximal end 190 of shaft 112 extends through the optional bushing 114. The bushing 114 includes an enlarged circular ring 192 which is captured in a corresponding circular groove 194 formed within the housing 102 from the first and second housing halves 104, 106 adjacent the respect bores 128, 134. The bushing 114 functions as a spacer to resist rotation of the central shaft 112 which extends therethrough. In this way, the bushing 114 functions to limit the travel of the knob based on the size limitations of the corresponding adjustable prosthetic anatomical device. The distal end 196 of the central shaft 112 is rotationally supported within the bore 138 provided at the distal end of the housing 102 by the ring 164 on the barrel 110 which is captured in an annular groove 198 formed within the housing halves 102, 106. Additional support of the shaft 112 is provided by the compression member 111 and portions of the housing 102.

Figure 4:
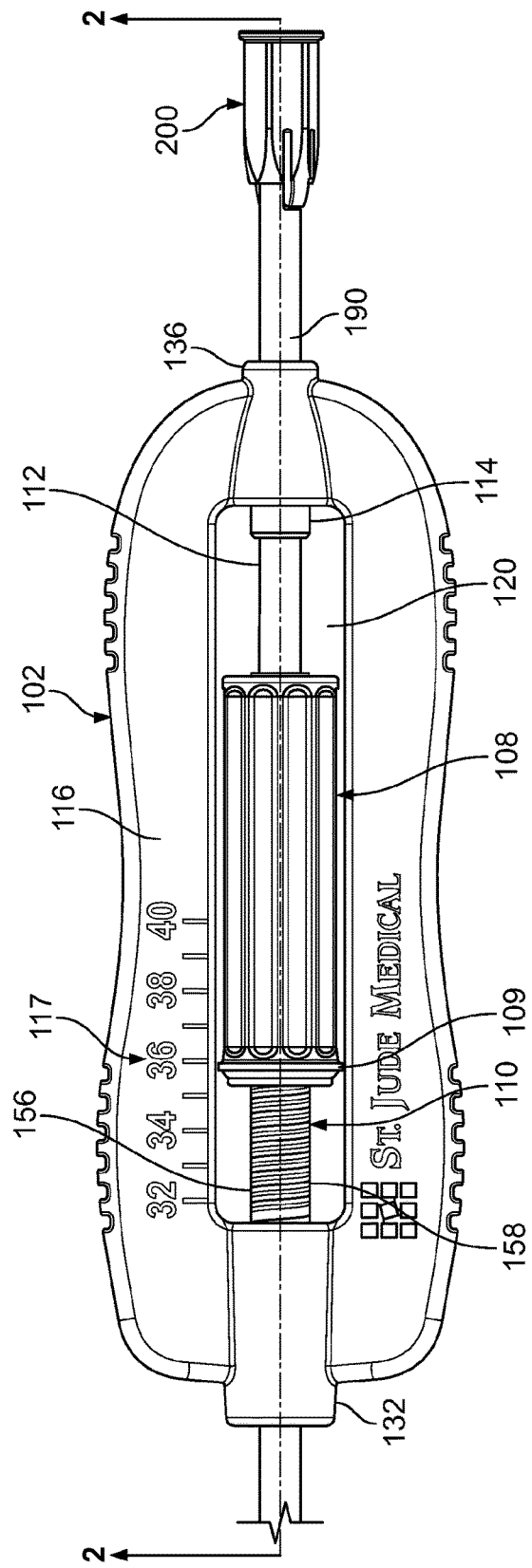
FIG. 4 is a top plan view of the assembled adjustment tool as shown in FIG. 1.

In the assembled form of the adjustment tool 100 in accordance with one embodiment as thus far described, such as shown in FIGS. 4 and 5, the knob 108 and barrel 110 are positioned within the opening 120 formed in the housing 102 by securing together the first and second housing halves 104, 106. The center shaft 112 passes through the bore 180 within the compression member 111, through the bore 162 in the barrel 110 and through the bore 144 within the knob 108. The knob 108 can be manipulated by ones fingers to cause its rotation about the barrel 110 by virtue of their threaded cooperation. As the knob 108 is rotated, the knob will advanced longitudinally within the opening 120 along the length of the barrel 110 to a degree related to the pitch of the threaded portions 146, 156 of the barrel and knob. During the manipulation of the knob 108, the barrel 110 is precluded from rotating by virtue of the projections 170 being capture within the notches 172 within the housing 102. Rotation of the knob 108 causes rotation of the central shaft 112, the rotation of which is retarded by the compression member 111. Compression of the elongated members 178 of the compression member 111 is maintained by the o-ring 186. The compression member 111 and o-ring 186 cooperate to prevent unintended rotation of the shaft. Accordingly, the shaft 112 can be rotated by a controlled amount by rotating the barrel 108. The rotation of the shaft 112 is operative for adjusting the opening size and/or shape of an annuloplasty ring or other anatomical device when coupled thereto.

Referring to FIGS. 5-8, there is shown a locking device constructed in accordance with one embodiment of the present invention generally designated by reference numeral 200. The locking device functions in accordance with one aspect thereof to removably attach the adjustment tool 100 to the implanted prosthetic anatomical device, such as an adjustable annuloplasty ring. The annuloplasty ring is thus maintained attached to the adjustment tool while being adjusted in situ by the surgeon thereby preventing inadvertent disconnection.

The locking device as illustrated is constructed to include an elongated shaft 202 having a threaded distal end 204, a hollow knob 206 and a hollow sleeve 208. The knob 206 can be constructed as a unitary cylindrical body having a first portion 210 of a first diameter and a second portion 212 of a larger second diameter. The end 214 of the second portion 212 generally has a noncylindrical shaped profile such as square, rectangular, polygonal, oval, triangular or the like. An elongated bore 216 extends through the knob 206 having a smaller restricted bore 218 extending through end 214 as shown in FIG. 10. The shaft 202 extends through the bore 216 having its end secured within the restricted bore 218. The cylindrical first portion 210 of the knob 206 is received within a bore 220 at the proximal end 221 of the shaft 112. The diameter of the first portion 210 is sized and shaped to enable rotation of the knob within the bore 220. A lip 224 is formed at the juncture of the first and second portions 210, 212 of the knob as a result of the different diameters. In accordance with the preferred embodiment, the knob 206 is constructed from surgical material such as titanium, stainless steel and the like.

The sleeve 208 as shown in FIGS. 7, 8 and 10 can be constructed as an elongated body 226 having a through bore 228. A configured portion 230 of the bore 228 adjacent the proximal end 232 of the sleeve 208 has a geometric shape complimentary to the geometric shape of end 214 of the knob 206. The end 214 of the knob 206 is slidingly received within the configured portion 230 and prevented from relative rotation by virtue of the complimentary noncircular shapes of the end 214 and configured portion 230. This construction keys the sleeve 208 to the knob 206 preventing relative rotation therebetween. The remaining portion of the bore 228 is sized and shaped to slidingly receive the remaining portions of the first and second portions 210, 212 of the knob 206, see FIGS. 10 and 12.

The distal portion 234 of the sleeve 208 is provided with at least one, and preferably at least two, elongated appendages 236 each preferably having an inwardly directed locking tab 238 at their free end. The appendages 236 are formed between spaced apart elongated slots 240 or other arrangements which provide the appendages with resiliency to enable their flexing during use of the locking tool 200 as to be described hereinafter. In this regard, the sleeve 208 can be constructed from suitable synthetic polymers such as those used in the construction of the compression member 111 as described with respect to the adjustment tool 100. In the preferred embodiment shown, two appendages 236 are provided arranged opposing one another. However, it is to be understood that a single appendage 236 provided with a locking tab 238 is contemplated, as well as more than two such appendages arranged circumferentially about the sleeve 208.

One or more openings 242 are provided adjacent the proximal end 221 of the central shaft 112. The openings 242 are sized, shaped and arranged to align with and receive the locking tabs 238 provided on the appendages 236. Accordingly, in the preferred embodiment, each locking tab 238 will be associated with at least one opening 242 for releasable receipt of the locking tab therein.

Referring to FIGS. 9-12, there will be described the operation of the locking device 200 in accordance with one embodiment of the present invention as thus far described. The primary function of the locking device is to provide the surgeon with the capability of releasable securing the adjustment tool 100 to an implanted prosthetic anatomical device by rotation of the knob 206. On the other hand, the central shaft 112 has its primary function to enable adjustment of the size and/or shape of the anatomical device by rotation of the knob 108 as previously described with respect to FIGS. 1-4. The sleeve 208 is adapted to slide longitudinally along the length of the knob 206 in keyed relationship whereby the locking tabs 238 on the appendages 236 are received within and released from the openings 242 on the proximal end 221 of the central shaft 112. The sleeve 208 is keyed to the knob 206 such that when the locking device 200 is arranged in its rearward unlocked position, rotation of the sleeve effects rotation of the knob 206, and enhance rotation of the shaft 202 which has a threaded tip 204 for releasable engagement with the anatomical device. When the sleeve 208 is arranged in its forward locked position, the locking device 200 prevents rotation of the knob 206 and shaft 202 to prevent disengagement of the adjustable tool 100 from the anatomical device.

Referring to FIGS. 9 and 10, the locking device 200 is shown in an unlocked position accomplished by sliding the sleeve 208 rearwardly whereby rotation of the sleeve 208 causes concurrent rotation of the knob 206, and enhance rotation of the shaft 202. As previously described, the knob 206 is keyed to the sleeve 208 as a result of the complimentary noncircular shapes of end 214 of the knob 206 and the configured portion 230 of the bore 228 of the sleeve 208. In the unlocked position of the locking device 200, the locking tabs 238 on the appendages 236 are not captured within the openings 242 in the central shaft 112. Rather, the locking tabs 238 are received about the first portion 210 of the knob 206 between the lip 224 and the proximal end 221 of the central shaft 112. This arrangement allows the keyed sleeve 208 and knob 206 combination to freely rotate disengage from the central shaft 112, thereby enabling rotation of shaft 202 for engagement and disengagement with the anatomical device.

The locking device 200 is shown in a locked position in FIGS. 11 and 12. The locked position is accomplished by sliding the sleeve 208 forward longitudinally along the length of the knob 206 until the locking tabs 238 are captured within the openings 242 in the central shaft 112. This action is facilitated by the appendages 236 being flexible and resilient so as to deflect radially outward when abutting the proximal end 221 of the central shaft 112. The proximal end 221 of the central shaft 112 maybe provided with a chamfered edge to facilitate displacement of the appendages 236. Accordingly, after the appendages 236 are expanded outwardly as they slide over the proximal end 221 of the central end 112, they return to their original orientation such that the locking tabs 238 are now received within the openings 242. The engagement of the locking tabs 238 with the openings 242 prohibit rotation of the sleeve 208, and enhance knob 206, thereby preventing disengagement of the adjustment tool 100 from the anatomical device being adjusted.

Figure 13:
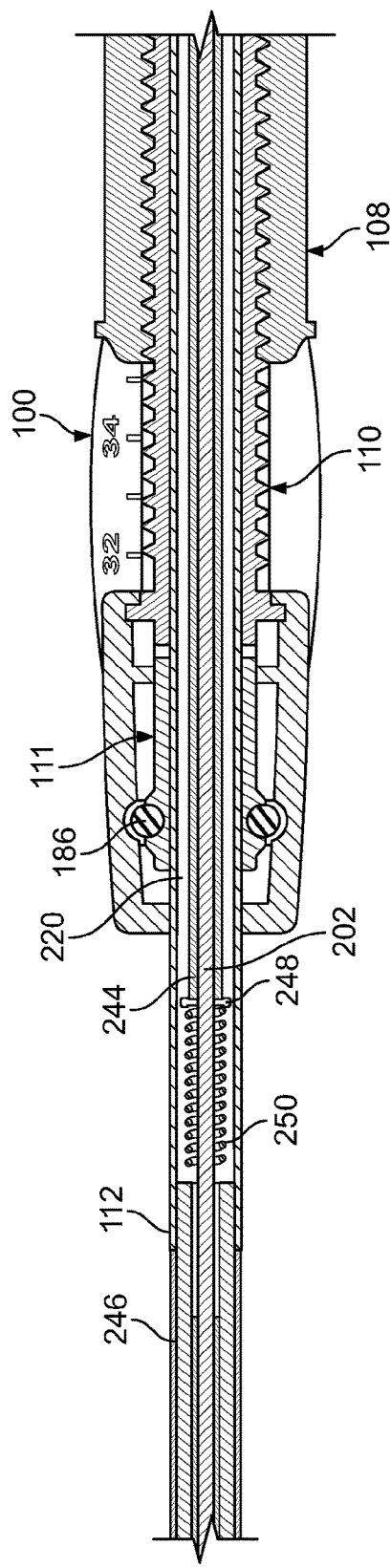
FIG. 13 is a cross-sectional view of the distal end of an adjustment tool incorporating a rotational locking device in accordance with one embodiment of the present invention.

In accordance with another aspect of the present invention as shown in FIG. 13, an elongated hypotube 244 is arranged concentric about shaft 202 extending through the adjustment tool 100 and into the bore 216 within the knob 206 of the locking device 200. The end of the hypotube 244 may be secured within the bore 216 of the knob 206, or otherwise be arranged in abutting engagement with a portion thereof. The shaft 202 extends longitudinally through an enlarged hypotube 246 which is attached to the free end of the central shaft 112.

The distal end of the hypotube 244 can optionally be provided with a flange 248. A compression spring 250 can be arranged extending longitudinally about a portion of the shaft 202 between the flange 248 and the proximal end of the hypotube 246. The spring 250 is arranged in compression thereby biasing the threaded distal end 204 of the shaft 202 into a released or non-engaged position with the anatomical device. This optional arrangement, facilitates detachment of the adjustable tool 100 after adjustment of the anatomical device.

Figure 14:
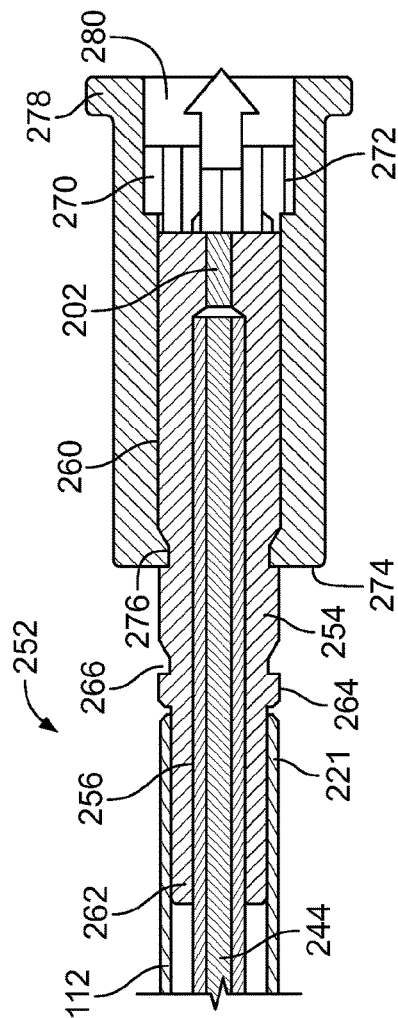
FIG. 14 is a cross-sectional view of a rotational locking device in accordance with another embodiment of the present invention shown in a locked position.
Figure 15:
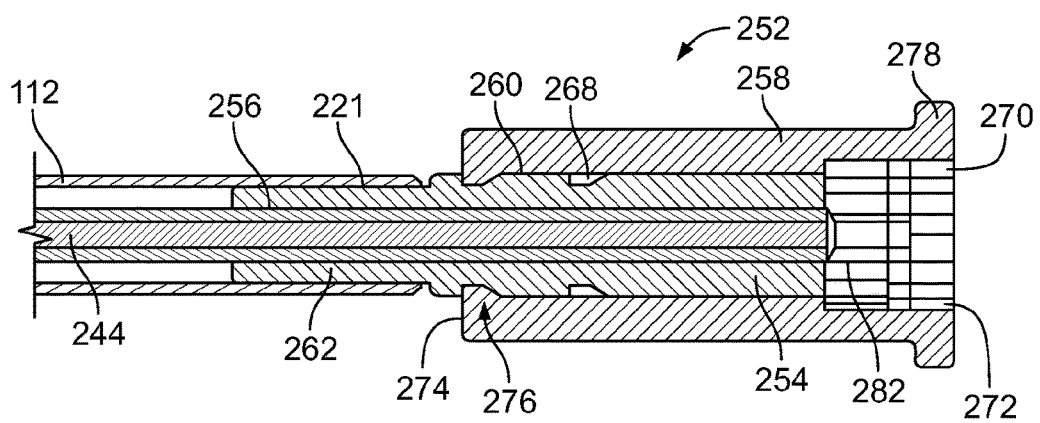
FIG. 15 is a cross-sectional view of the rotational locking device of FIG. 14 shown in an unlocked position.

Referring to FIGS. 14 and 15, there will now be described a locking device 252 constructed in accordance with another embodiment of the present invention. The locking device 252 includes an elongated generally cylindrical knob 254 having an elongated bore 256 extending therethrough, and a generally elongated cylindrical sleeve 258 having a bore 260 extending therethrough. The knob 254 has a distal end 262 configured to be rotationally received within the proximal end 221 of the central shaft 112. Insertion of the knob 254 is restricted by an abutment 264 circumscribing a portion of the knob. The remaining portion of the knob is slidingly received longitudinally within the bore 260 of the sleeve 258. A pair of spaced apart annular grooves 266, 268 are arranged circumferentially about the knob 254 outwardly of the abutment 264. Although the grooves are described as annular grooves, it is contemplated that the grooves may be discontinuous or that the grooves may be constructed in other forms such as openings, raised elements and the like which will be understood from the application of the grooves to be described hereinafter. The proximal end 270 of the knob is constructed in the form of a locking element 272. The locking element 272 can be constructed as a configured member, such as a plurality of gear teeth, in the form of a noncylindrical shape such as square, polygonal, oval and the like. The end of the shaft 202 is attached to the knob 254, such as at its proximal end 270.

The sleeve 258 at its distal end 274 is formed to include one or more tabs 276 which extend radially inwardly. The tabs 276 may be constructed in a similar manner as the locking tabs 238 as previously described with respect to the locking device 200. In this regard, the sleeve 258 may be provided with appendages formed by elongated slots as thus far described with respect to the locking device 200. The tabs 276 are configured to be releasably engageable within the grooves 266, 268 by longitudinally sliding the sleeve 258 along the length of the knob 254.

The bore 260 of the sleeve is formed at its proximal end 278 with a nonengagement portion 280 and an inwardly provided portion forming a locking element 282. The locking element 282 is configured to cooperate with the locking element 272 on the knob 254. In this regard, the locking element 282 is preferably constructed as a complimentary structure, such as meshing gears, or a complimentary shaped structure. Accordingly, when the locking elements 272, 282 are engaged, rotation of the sleeve 258 will cause rotation of the knob 254. On the other hand, the nonengagement portion 280 is configured so as not to engage the locking element 272 of the knob 254 when received within the nonengagement portion.

As shown in FIG. 14, the locking device 252 is arranged in a locked orientation whereby rotation of the sleeve 258 causes rotation of the knob 254. In the locked orientation, the sleeve 258 is arranged rearwardly along the knob 254 such that the tabs 276 are received within the groove 268, and the locking elements 272, 282 are maintained engaged with one another. Rotation of the sleeve 258 effects rotation of the shaft 202 to allow for the attachment and disengagement of the adjustment tool 100 to an anatomical device.

The locking device 252 is shown in an unlocked orientation in FIG. 15. In this regard, the sleeve 258 has been displaced longitudinally forward on the knob 254 whereby the tabs 276 are received within the groove 266. In this orientation, the locking element 272 at the proximal end of the knob 270 is received within the nonengagement portion 280 of the sleeve 258. Rotation of the sleeve 258 will not effect rotation of the knob 254, and therefore, will not effect rotation of the shaft 202.

As best shown in FIG. 4, in one exemplary embodiment, housing 102 may include a scale 117. Knob 108 may also include a pointer 109. Pointer 109 may be arranged on knob 108 and adapted to align with scale 117. Scale 117 and pointer 109 allow a surgeon using adjustment tool 100 to determine the degree to which the size of the adjustable annuloplasty ring has been adjusted during the annuloplasty procedure. In one embodiment, pointer 109 may be a band at least partially circumscribing knob 108. In another embodiment, pointer 109 may include one or more arrows arranged on knob 108. Preferably, pointer 109 is arranged adjacent a distal end of knob 108, but may alternatively be arranged at another location along knob 108 in other embodiments. Furthermore, another embodiment may include multiple pointers 109 arranged at various positions along knob 108.

In one embodiment, scale 117 is printed on housing 102. In other embodiments, scale 117 may, for example, be etched, engraved, embossed, or molded to housing 102. Scale 117 may also be raised on or recessed into housing 102. In another embodiment, scale 117 may include an electronic display (not shown) provided on housing 102. In another embodiment, scale 117 may be provided on one or more labels that can be permanently or temporarily affixed to housing 102.

Scale 117 provides the surgeon with a reference to determine the degree to which the size of the adjustable annuloplasty ring has been adjusted during the procedure and whether to adjust the size of the annuloplasty ring further. By referring to scale 117, the surgeon may determine the actual annuloplasty ring size or size relative to scale 117 at the beginning of the annuloplasty procedure and the adjustments that have been performed relative to that size throughout the procedure. The surgeon may therefore determine the degree to which the size of the adjustable annuloplasty ring has been adjusted, and may decide whether to make a further adjustment thereto. Moreover, if the surgeon decides to make a further adjustment, scale 117 may also allow the surgeon to determine the magnitude of the further adjustment that is necessary or preferred. In one embodiment, scale 117 may also indicate the desired size of the annuloplasty ring, which may be determined prior to the annuloplasty procedure, which may allow the surgeon to compare the size of the annuloplasty ring at a given time during the procedure with the predetermined desired size.

In the exemplary embodiment shown, scale 117 is a Seguin sizing scale. However, in other embodiments, scale 117 may be another type of scale. For example, in other embodiments, scale 117 may list one or more dimensions of the adjustable prosthetic anatomical device corresponding to different positions along scale 117. In some embodiments, the dimension(s) listed on scale 117 may be the diameter, circumference, length of an anterior/posterior axis, length of a commissure-to-commissure (C/C) axis, and/or another dimension of the device. In one embodiment, scale 117 indicates the dimension(s) in millimeters. In other embodiments, scale 117 may indicate the dimension(s) in inches or any other appropriate unit of measure. Furthermore, in other embodiments, scale 117 may be a set of letters, dashes, tick marks, indicia, or other symbols indicating the relative position of pointer 109 and, therefore, the size of the adjustable prosthetic anatomical device, which may be the actual size or the size relative to scale 117. In other embodiments, multiple tools 100 may be provided, with the scale 117 provided on each tool pertaining to a different range of sizes. In different embodiments, some of the ranges may partially overlap with one another; however, in other embodiments, multiple tools 100 may each cover separate size ranges.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tool for manipulating an adjustable device comprising:
   a cylinder;
   a knob rotationally engaged about the cylinder;
   a shaft extending through the cylinder coupled to the knob, whereby rotation of the knob about the cylinder causes rotation of the shaft;
   a housing supporting the shaft for rotation by the knob; and
   a member arranged within the housing directly engaging a portion of the shaft for retarding rotation of the shaft.

2. The tool of claim 1, wherein the member comprises a compression member and the cylinder are a one piece integral unit.

3. The tool of claim 1, wherein the member comprises a plurality of appendages arranged circumferentially about the shaft.

4. The tool of claim 3, further including an o-ring arranged about the plurality of appendages, wherein the o-ring provides a compressive force compressing the plurality of appendages against the shaft for retarding rotation of the shaft.

5. The tool of claim 3, further including at least one tab extending from the cylinder in engagement with a portion of the housing, the at least one tab preventing rotation of the cylinder upon rotation of the knob thereabout.

6. The tool of claim 5, wherein the housing comprises a handle having opposing ends and an elongated opening therebetween, a first bore extending through one end of the handle in communication with the opening and a second bore extending through another end of the handle in communication with the opening.

7. The tool of claim 6, wherein the plurality of appendages and the o-ring are arranged within the first bore of the handle.

8. The tool of claim 6, wherein one end of the shaft is rotationally supported in the first bore and another end of the shaft is rotationally supported in the second bore.

9. A tool for manipulating an adjustable device comprising:
   an externally threaded elongated barrel having a distal end and a proximal end;
   an internally threaded knob rotationally coupled about the barrel;
   a shaft extending through the barrel having a portion thereof attached to the knob, whereby rotation of the knob causes rotation of the shaft;
   a compression member extending from the distal end of the barrel overlaying the shaft;
   a compression element compressing the compression member against the shaft, whereby rotation of the shaft is retarded; and
   a housing supporting the rotation of the shaft by rotation of the knob.

10. The tool of claim 9, further including at least one tab extending from the barrel in engagement with a portion of the housing, the at least one tab preventing rotation of the barrel upon rotation of the knob thereabout.

11. The tool of claim 9, wherein the compression member and the barrel are a one piece integral unit.

12. The tool of claim 9, wherein the compression member comprises a plurality of appendages arranged circumferentially about the shaft.

13. The tool of claim 12, wherein the compression element comprises an o-ring arranged about the plurality of appendages, wherein the o-ring provides a compressive force compressing the plurality of appendages against the shaft for retarding rotation of the shaft.

14. The tool of claim 9, wherein the housing compresses a handle having opposing ends and an elongated opening therebetween, a first bore extending through one end of the handle in communication with the opening and a second bore extending through another end of the handle in communication with the opening.

15. The tool of claim 14, wherein the compression member and compression element are arranged with the first bore of the handle.

16. The tool of claim 15, wherein one end of the shaft is rotationally supported in the first bore and another end of the shaft is rotational supported in the second bore.

17. An adjustment tool for adjusting the size of an annuloplasty ring, the tool comprising:
   a handle having a distal end and a proximal end, the handle having an elongated central opening, a first bore extending through the distal end of the handle in communication with the opening, and a second bore extending through the proximal end in communication with the opening;
   an externally threaded hollow barrel arranged within the opening of the handle, the barrel having a fixed axis in alignment with the first and second bores;
   an internally threaded knob rotationally engaged about the barrel within the opening, the knob having a rotational axis in alignment with the fixed axis of the barrel;
   a central shaft extending along the rotational axis through the first bore and through the barrel into the knob, the shaft having a portion attached to the knob whereby rotation of the knob about the barrel causes rotation of the shaft about the rotational axis;
   a plurality of appendages extending from the barrel into the first bore surrounding at least a portion of the shaft; and
   a compression element compressing the plurality of appendages about the shaft whereby rotation of the shaft is retarded.

18. The tool of claim 17, wherein the plurality of appendages and the barrel are a one piece integral unit.

19. The tool of claim 17, wherein the compression element comprises an o-ring.

20. The tool of claim 17, further including at least one tab extending from the barrel in engagement with a portion of the housing, the at least one tab preventing rotation of the barrel upon rotation of the knob thereabout.

21. A tool for manipulating an adjustable device comprising:
   a cylinder;
   a knob rotationally engaged about the cylinder;
   a shaft extending through the cylinder coupled to the knob, whereby rotation of the knob about the cylinder causes rotation of the shaft;
   a housing supporting the shaft for rotation by the knob; and
   a member arranged within the housing engaging a portion of the shaft for retarding rotation of the shaft, wherein the member comprises a compression member and the cylinder are a one piece integral unit.

* * * * *